(12) United States Patent
Mahajan et al.

(10) Patent No.: US 8,403,830 B2
(45) Date of Patent: Mar. 26, 2013

(54) RHYTHM DISCRIMINATION ENHANCEMENT—AV DRIVE

(75) Inventors: Deepa Mahajan, Circle Pines, MN (US); Yanting Dong, Shoreview, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 64 days.

(21) Appl. No.: 13/196,491

(22) Filed: Aug. 2, 2011

(65) Prior Publication Data

US 2012/0035491 A1 Feb. 9, 2012

Related U.S. Application Data

(60) Provisional application No. 61/371,398, filed on Aug. 6, 2010.

(51) Int. Cl.
*A61B 1/00* (2006.01)
(52) U.S. Cl. ........................................ 600/118
(58) Field of Classification Search .................. 600/118, 600/119
See application file for complete search history.

(56) References Cited

U.S. PATENT DOCUMENTS

| | | | |
|---|---|---|---|
| 4,872,459 A | 10/1989 | Pless et al. | |
| 4,880,005 A | 11/1989 | Pless et al. | |
| 5,129,393 A * | 7/1992 | Brumwell | 607/9 |
| 5,814,085 A | 9/1998 | Hill | |
| 6,058,328 A | 5/2000 | Levine et al. | |
| 6,179,865 B1 | 1/2001 | Hsu et al. | |
| 6,314,321 B1 | 11/2001 | Morris | |
| 6,493,579 B1 | 12/2002 | Gilkerson et al. | |
| 6,522,917 B1 | 2/2003 | Hsu et al. | |
| 6,567,691 B1 | 5/2003 | Stadler | |
| 6,636,764 B1 | 10/2003 | Fain et al. | |
| 6,681,134 B2 | 1/2004 | Morris et al. | |
| 6,708,058 B2 | 3/2004 | Kim et al. | |
| 6,748,269 B2 | 6/2004 | Thompson et al. | |
| 6,889,079 B2 | 5/2005 | Bocek et al. | |
| 6,980,860 B2 | 12/2005 | Stadler et al. | |
| 7,031,764 B2 | 4/2006 | Schwartz et al. | |
| 7,050,852 B2 | 5/2006 | Zhu et al. | |
| 7,062,316 B2 | 6/2006 | Hsu et al. | |

(Continued)

FOREIGN PATENT DOCUMENTS

WO WO-2007133762 A1 11/2007

OTHER PUBLICATIONS

Aliot, Etienne, et al., "Arrhythmia detection by dual-chamber implantable cardioverter defibrillators. A review of current algorithms", Europace, 6(4), (Jul. 2004), 273-86.

(Continued)

*Primary Examiner* — George Manuel
(74) *Attorney, Agent, or Firm* — Schwegman Lundberg & Woessner, P.A.

(57) ABSTRACT

An apparatus comprises an implantable cardiac signal sensing circuit and a controller circuit. The implantable cardiac signal sensing circuit provides a sensed depolarization signal from a ventricle and a sensed depolarization signal from an atrium. The controller circuit includes a one-to-one detector circuit and a tachyarrhythmia discrimination circuit. The one-to-one detector circuit measures cardiac depolarization intervals of the atrium and the ventricle and determines whether a relationship of atrial depolarizations to ventricular depolarizations is substantially one-to-one. The tachyarrhythmia discrimination circuit increments a counter when detecting a shortening or prolonging of a V-V interval that immediately precedes the same shortening or prolonging of an A-A interval, classifies the episode as VT according to the counter, and provides the classification of the tachyarrhythmia episode to a user or process.

20 Claims, 8 Drawing Sheets

U.S. PATENT DOCUMENTS

| | | |
|---|---|---|
| 7,162,300 B2 | 1/2007 | van Groeningen et al. |
| 7,174,209 B2 | 2/2007 | Thompson et al. |
| 7,203,535 B1 | 4/2007 | Hsu et al. |
| 7,203,538 B2 | 4/2007 | Schwartz et al. |
| 7,212,855 B1 | 5/2007 | Kroll et al. |
| 7,225,020 B1 | 5/2007 | Kroll et al. |
| 7,313,436 B2 | 12/2007 | Hess |
| 7,321,794 B2 | 1/2008 | Thacker et al. |
| 7,346,388 B2 | 3/2008 | Elahi et al. |
| 7,363,081 B1 | 4/2008 | Kroll et al. |
| 7,440,799 B2 | 10/2008 | Morris |
| 7,515,956 B2 | 4/2009 | Thompson et al. |
| 7,537,569 B2 | 5/2009 | Sarkar et al. |
| 7,606,620 B2 | 10/2009 | Gilkerson et al. |
| 7,664,553 B2 | 2/2010 | Earle |
| 2006/0287684 A1 | 12/2006 | Baynham et al. |
| 2007/0049835 A1 | 3/2007 | Goode |
| 2007/0135852 A1 | 6/2007 | Kim et al. |
| 2007/0167987 A1 | 7/2007 | Schwartz et al. |
| 2007/0197928 A1 | 8/2007 | Kim et al. |
| 2007/0219456 A1 | 9/2007 | Thompson |
| 2008/0281370 A1 | 11/2008 | Lin et al. |
| 2009/0118781 A1 | 5/2009 | Morris |
| 2009/0264716 A1 | 10/2009 | Shuros et al. |

OTHER PUBLICATIONS

Jongnarangsin, K., et al., "Utility of tachycardia cycle length variability in discriminating atrial tachycardia from ventricular tachycardia", Heart Rhythm, 7(2), (Feb. 2010), 225-228.

Keung, Edward, "SVT Discrimination Algorithm", San Francisco VA Hospital, (Jan. 23, 2009), 19 pgs.

Swerdlow, C. D, et al., "Advanced ICD troubleshooting: Part I.", Pacing Clin Electrophysiol., 28(12), (Dec. 2005), 1322-46.

\* cited by examiner

RHYTHM DISCRIMINATION ENHANCEMENT—AV DRIVE

CROSS-REFERENCE TO RELATED APPLICATIONS

This application claims the benefit of U.S. Provisional Application No. 61/371,398, filed on Aug. 6, 2010, under 35 U.S.C. §119(e), which is incorporated herein by reference in its entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. Some IMDs detect abnormally rapid heart rate, or tachyarrhythmia. Tachyarrhythmia includes ventricular tachycardia (VT) and supraventricular tachycardia (SVT). Tachyarrhythmia also includes rapid and irregular heart rate, or fibrillation, including ventricular fibrillation (VF).

When detected, ventricular tachyarrhythmia can be terminated with high-energy shock therapy delivered with an ICD. Cardioversion/defibrillation therapy can cause patient discomfort and consumes a relatively large amount of battery power which may lead to a shortened useful device lifetime.

Overview

This document relates generally to systems, devices, and methods for monitoring cardiac electrophysiological parameters of a patient or subject. Episodes of atrial and ventricular tachyarrhythmia are also monitored.

An apparatus example includes an implantable cardiac signal sensing circuit, configured to provide a sensed depolarization signal from a ventricle and a sensed depolarization signal from an atrium; and a controller circuit communicatively coupled to the implantable cardiac signal sensing circuit. The controller circuit includes a one-to-one detector circuit and a tachyarrhythmia discrimination circuit. The one-to-one detector circuit is configured to measure cardiac depolarization intervals of the atrium and the ventricle and determine whether a relationship of atrial (A-A) depolarizations to ventricular (V-V) depolarizations is substantially one-to-one. The tachyarrhythmia discrimination circuit is configured to detect an episode of tachyarrhythmia while the relationship atrial depolarizations to ventricular depolarizations is substantially one-to-one, increment a first counter when detecting one of a shortening or prolonging of a V-V interval that is immediately preceded by the same one of a detected shortening or prolonging of an A-A interval during the episode, increment a second counter when detecting one of a shortening or prolonging of an A-A interval during the episode that is immediately preceded by the same one of a shortening or prolonging of a V-V interval and an interval from a ventricular depolarization to an atrial depolarization (V-A) is greater than a specified threshold V-A interval value, classify the episode as VT when the count of the second counter exceeds the count of the first counter by a specified threshold count, and provide the classification of the tachyarrhythmia episode to a user or process.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document discusses systems and methods for improved detection of cardiac events by an IMD. Specifically systems and methods for improved discrimination or classification of tachyarrhythmia by an IMD are described.

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
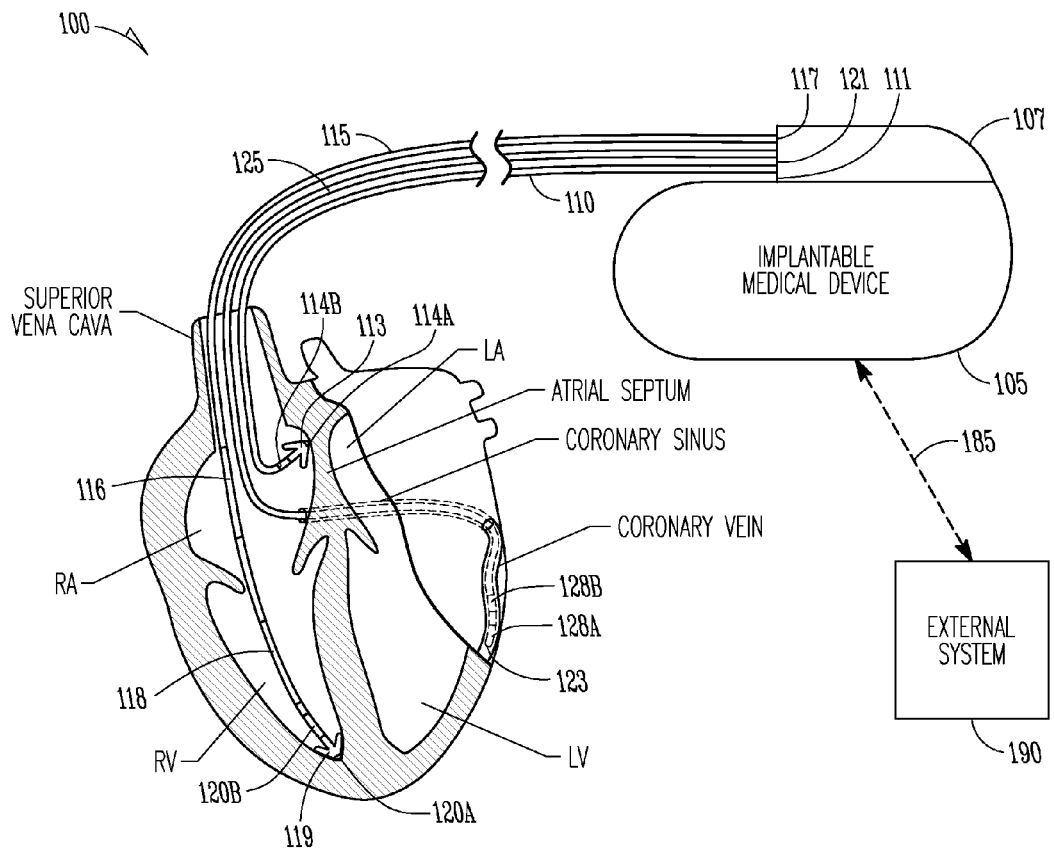
FIG. 1 is an illustration of portions of a system that uses an IMD.

FIG. 1 is an illustration of portions of a system 100 that uses an IMD 105. Examples of the IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown can be used to detect and treat a cardiac arrhythmia such as tachyarrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed housing or "can." System 100 also typically includes an IMD programmer or other external system 190 that communicates one or more wireless signals 185 with the IMD 105, such as by using radio frequency (RF) or one or more other telemetry signals.

The example shown includes right atrial (RA) lead 110 having a proximal end 111 and a distal end 113. Proximal end 111 is coupled to a header connector 107 of the IMD 105. Distal end 113 is configured for placement in the RA in or near the atrial septum. RA lead 110 may include a pair of bipolar electrodes, such as an RA tip electrode 114A and an RA ring electrode 114B. RA electrodes 114A and 114B are incorporated into the lead body at distal end 113 for placement in or near the atrial septum, and are each electrically coupled to IMD 105 through a conductor extending within the lead body. The RA lead is shown placed in or near the atrial septum, but the RA lead may be placed in the atrial appendage.

The example shown also includes right ventricular (RV) lead 115 having a proximal end 117 and a distal end 119. Proximal end 117 is coupled to header connector 107. Distal end 119 is configured for placement in the RV. RV lead 115 may include one or more of a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA or the superior vena cava. Defibrillation electrode 118 is incorporated into the lead body near distal end 119 for placement in the RV. RV electrodes 120A and 120B may form a bipolar electrode pair and are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or an electrode formed on the can of IMD 105 allow for delivery of cardioversion/defibrillation pulses to the heart.

RV tip electrode 120A, RV ring electrode 120B, and/or an electrode formed on the can of IMD 105 allow for sensing an RV electrogram indicative of RV depolarizations and delivering RV pacing pulses. Any combination of RV tip electrode 120A, RV ring electrode 120B, and an electrode formed on the can of IMD 105, or other ventricular electrode can be referred to as a ventricular channel. RA tip electrode 114A, RA ring electrode 114B, and/or an electrode formed on the can of IMD 105 allow for sensing an RA electrogram indicative of RA depolarizations and delivering RA pacing pulses. Any combination of RA tip electrode 114A, RA ring electrode 114B, electrode formed on the can of IMD 105, and/or other atrial electrode can be referred to as an atrial channel. Sensing channels can also include defibrillation electrodes. Any combination of electrodes that includes the proximal defibrillation electrode 116, the distal defibrillation electrode 118, and/or an electrode formed on the can of the IMD 105 can be referred to as a shock channel.

Sensing and pacing allows the IMD 105 to adjust timing of the heart chamber contractions. In some device examples, IMD 105 can adjust the timing of ventricular contractions with respect to the timing of atrial contractions delay by sensing a contraction in the RA and pacing the RV at the desired atrial-ventricular (AV) delay time.

Also shown is a left ventricular (LV) lead 125. LV lead 125 is a coronary pacing and/or sensing lead that includes an elongate lead body having a proximal end 121 and a distal end 123. Proximal end 121 is coupled to header connector 107. Distal end 123 is configured for placement or insertion in the coronary vein. LV lead 125 may include an LV ring or tip electrode 128A and an LV ring electrode 128B. The distal portion of LV lead 125 is configured for placement in the coronary sinus and coronary vein such that LV electrodes 128A and 128B are placed in the coronary vein. LV electrodes 128A and 128B may form a bipolar electrode pair and are incorporated into the lead body at distal end 123 and each electrically coupled to IMD 105 through a conductor extending within the lead body. LV tip electrode 128A, LV ring electrode 128B, and/or an electrode formed on the can of IMD 105 allow for sensing an LV electrogram indicative of LV depolarizations and delivering LV pacing pulses. Any combination of LV tip electrode 128A, LV ring electrode 128B, and/or electrode formed on the can of IMD 105, and/or other ventricular electrode can also be referred to as a ventricular channel.

Other forms of electrodes include meshes and patches, which may be applied to one or more portions of heart, or which may be implanted in one or more other areas of the body to help "steer" electrical current produced by IMD 105 in FIG. 1. The IMDs may be configured with a variety of electrode arrangements, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). Monitoring of electrical signals related to cardiac activity may provide early, if not immediate, diagnosis of cardiac disease.

Typically, cardioverter defibrillators detect tachyarrhythmia by first detecting a rapid heart rate. Detection enhancements are sometime used to further distinguish or classify the detected arrhythmia. A detection enhancement example includes determining whether the rate detected in a ventricle (V Rate) is greater than the rate detected in an atrium (A Rate) by a specified rate threshold (e.g., V Rate>A Rate by more than ten beats per minute, or 10 bpm). This is often an indication that the arrhythmia is VT. However, sometimes the enhancements fail to accurately distinguish VT from SVT, especially during a tachyarrhythmia episode when ventricular events occur about one-to-one with atrial events during the tachyarrhythmia episode.

To improve classification of detected tachyarrhythmia, determining whether events in an atrium are "driving" events sensed in a ventricle or whether events in a ventricle are driving events sensed in an atrium can improve detection and discrimination of tachyarrhythmia.

Figure 2:
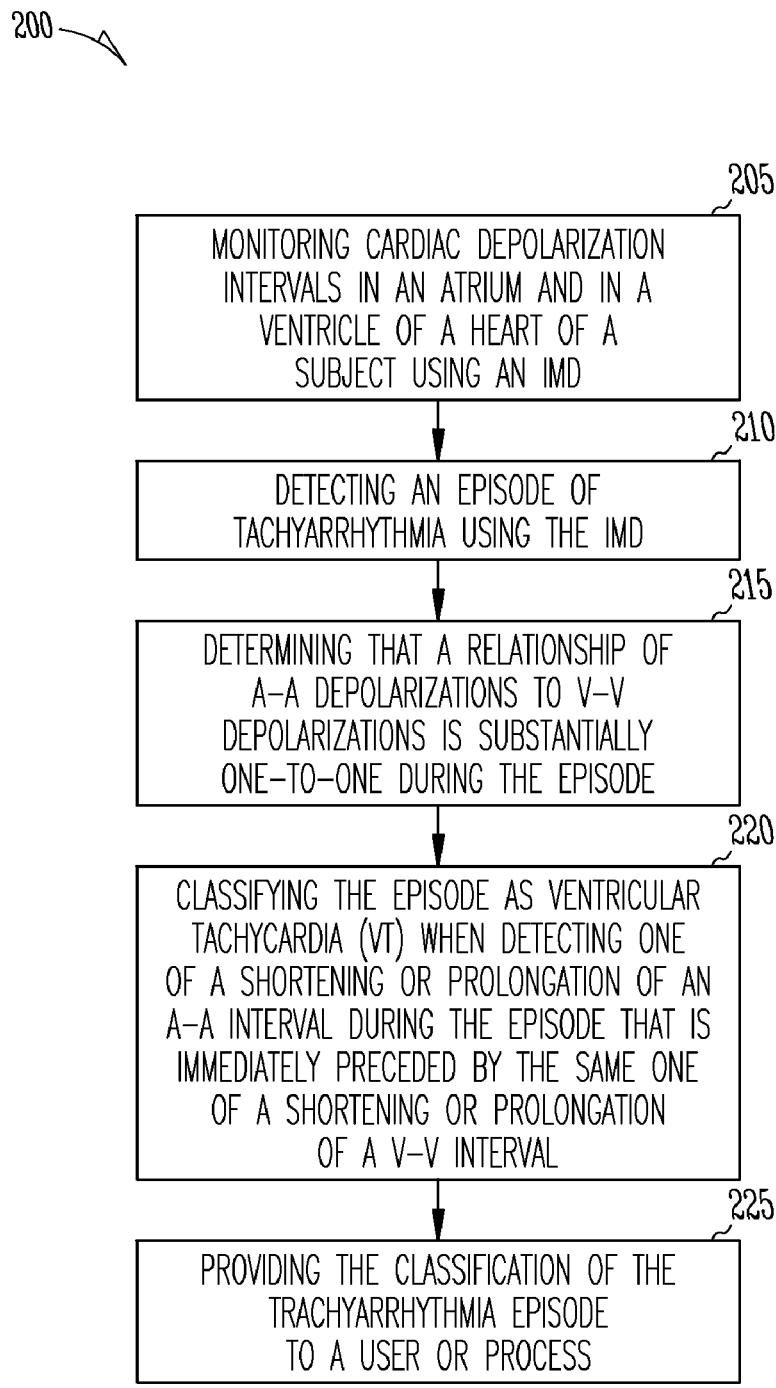
FIG. 2 is a flow chart of an example of a method of classifying a detected tachyarrhythmia.

FIG. 2 is a flow chart of an example of a method 200 of classifying a detected tachyarrhythmia. At block 205, cardiac depolarization intervals are monitored in an atrium and in a ventricle of a heart of a subject using an IMD.

At block 210, an episode of tachyarrhythmia is detected using the IMD. In some examples, the episode is detected when a ventricular depolarization rate is detected that exceeds a specified lowest tachyarrhythmia detection rate. In some examples, the episode is detected when a specified number of sensed ventricular depolarization intervals are less than a specified tachyarrhythmia detection threshold interval value. In some examples, detection parameters are specified by programming the parameters into the device.

At block 215, it is determined whether the relationship of sensed atrial depolarizations to sensed ventricular depolarizations is substantially one-to-one during the episode. In some examples, ventricular events are deemed to occur substantially one-to-one with atrial events during the episode when the number of ventricular depolarizations differs from the number of atrial depolarizations by less than a specified threshold depolarization difference value (e.g., 2 or less) during the tachyarrhythmia episode. Stated another way, the episode is deemed to be a one-to-one episode when for almost every atrial event there is a ventricular event and for almost every ventricular event there is an atrial event. In some examples, ventricular events are deemed to occur substantially one-to-one with atrial events during a tachyarrhythmia episode when the detected ventricular rate differs from the detected atrial rate by less than a specified rate difference (e.g., 10 bpm). In some examples, ventricular events are deemed to occur substantially one-to-one with atrial events during the tachyarrhythmia episode when measured ventricular-to-ventricular (V-V) intervals differ from measured atrial-to-atrial (A-A) intervals by less than a specified threshold interval value during the onset episode.

At block 220, the A-A intervals and the V-V intervals are monitored during the episode to determine if there is any change in the intervals. In particular, the monitoring looks for a change in one or both of an A-A interval and a V-V interval that exceeds a specified threshold interval change value (e.g., 20 milliseconds, or ms). If there is a change, it is determined whether the change is a shortening or a prolonging from the previous intervals and it is determined which heart chamber first experienced the change in depolarization intervals. The episode is then classified using the information about the change.

The episode is classified as VT when detecting one of a shortening or prolonging of an A-A interval during the episode, and the A-A interval shortening or prolonging is immediately preceded by substantially the same shortening or prolonging of a V-V interval. In some examples, the change is determined to be substantially the same between the two chambers when a measured difference between the V-V interval and the A-A interval is less than a specified threshold interval difference value. In certain examples, the threshold interval difference value is 20 ms. In certain examples, the threshold interval difference value is 50 ms.

In some examples, the episode is classified as supra-ventricular tachycardia (SVT) when the measured V-V interval change during the episode is immediately preceded by the A-A interval change and the difference between the A-A interval change and the V-V interval change is less than the specified interval change threshold value. In some examples, shortening or prolonging of more than one A-A and V-V interval is required before the episode is classified as SVT or VT.

Figure 3A:
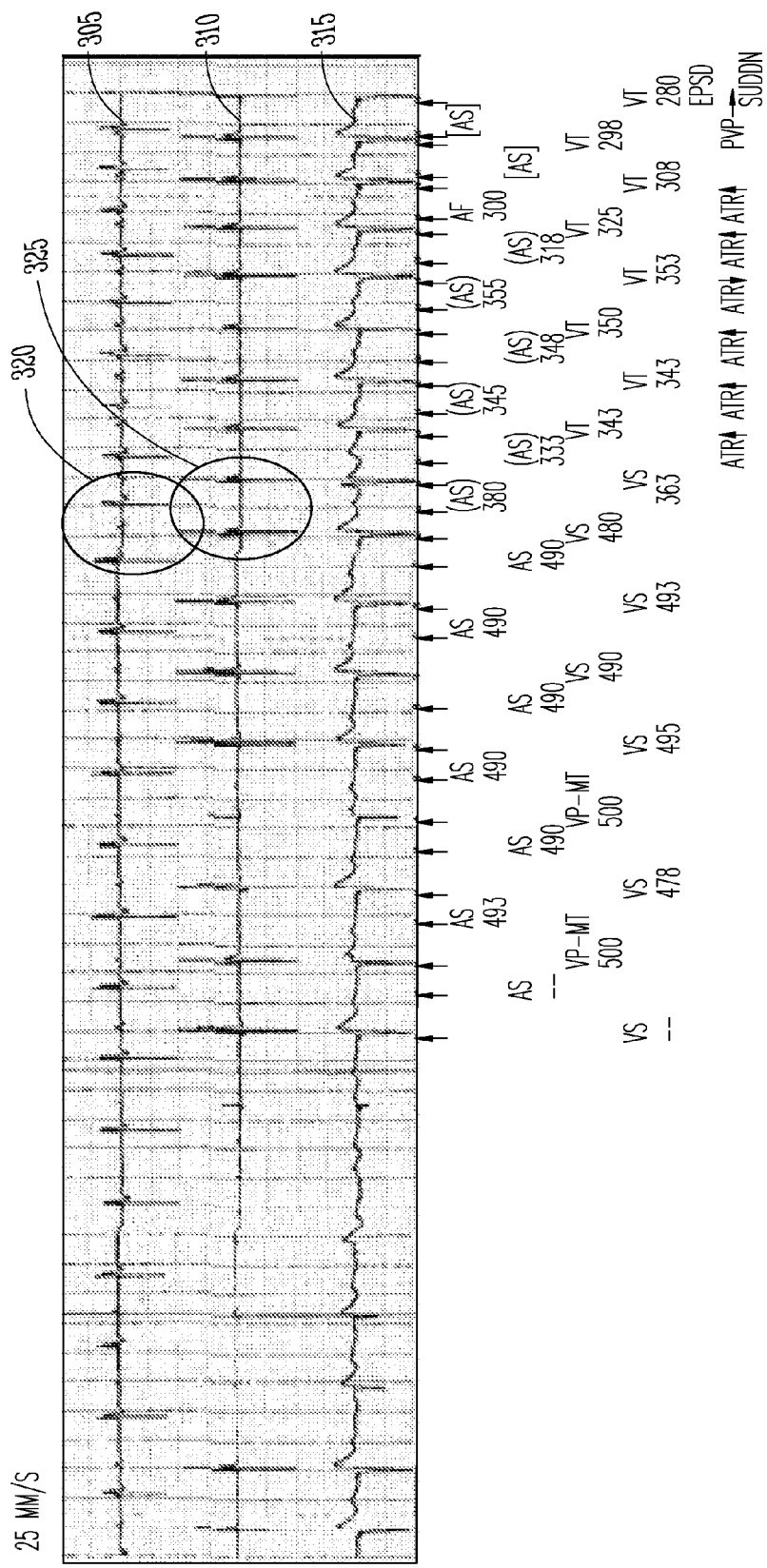
FIGS. 3A and 3B show examples of electrograms sensed during a tachyarrhythmia onset episode.
Figure 3B:
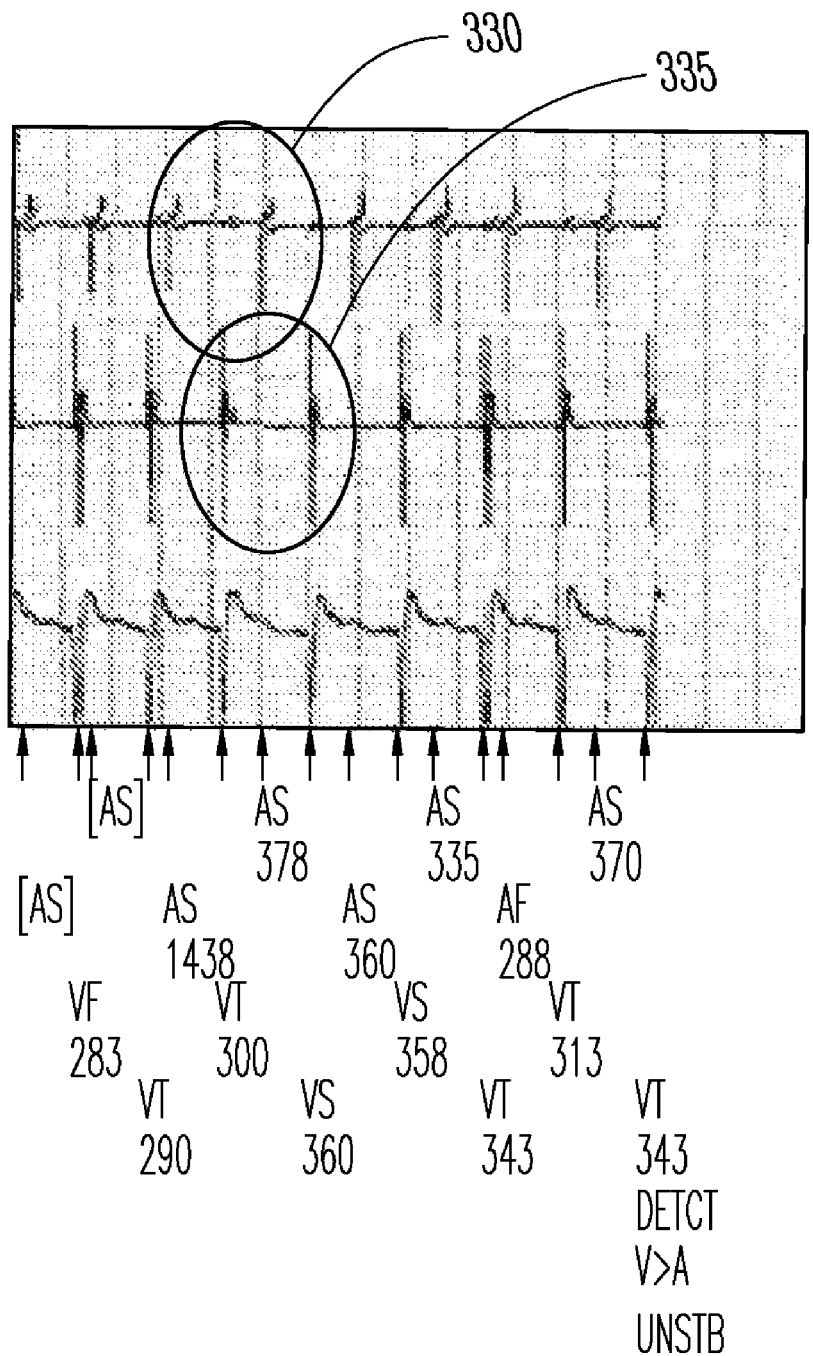

FIGS. 3A and 3B show examples of electrograms sensed during a tachyarrhythmia onset episode. In FIG. 3A, the top trace 305 is an electrogram sensed using an atrial channel. The middle trace 310 is an electrogram sensed using a ventricular channel, and the bottom trace 315 is an electrogram sensed using a shock channel. The electrograms show an example of depolarization interval shortening (320, 325). FIG. 3B shows an example of depolarization interval prolongation (330, 335). Note that the depolarizations in the atrium occur one-to-one with the depolarizations in the ventricle. In FIG. 3A, because the shortening 320 in the atrium precedes the shortening 325 in the ventricle and because the shortening is substantially the same in the intervals, the episode is classified as SVT. Similarly, in FIG. 3B, because the prolonging 330 in the atrium precedes the prolonging 335 in the ventricle and because the prolonging is substantially the same in the intervals, the episode is also classified as SVT.

In some examples, when the V-V intervals and the A-A intervals do not change during the episode, or do not change for specified duration of time or heartbeats, the episode may be classified as sinus tachycardia (ST). In some examples, if there is no detected difference between the V-V interval durations and the A-A interval durations during the tachyarrhythmia episode, or the detected difference is less than the specified interval change threshold value, the episode is classified as ST. In some examples, when the episode is initially classified as ST, other detection enhancements are activated to confirm ST.

Returning to FIG. 2 at block 225, the classification of the tachyarrhythmia episode is provided to a user or process. The process may be executing on a processor such as a microprocessor. The classification may be used to initiate or inhibit delivery of anti-tachyarrhythmia therapy, or the classification may be communicated to a process executing on a second device.

Figure 4:
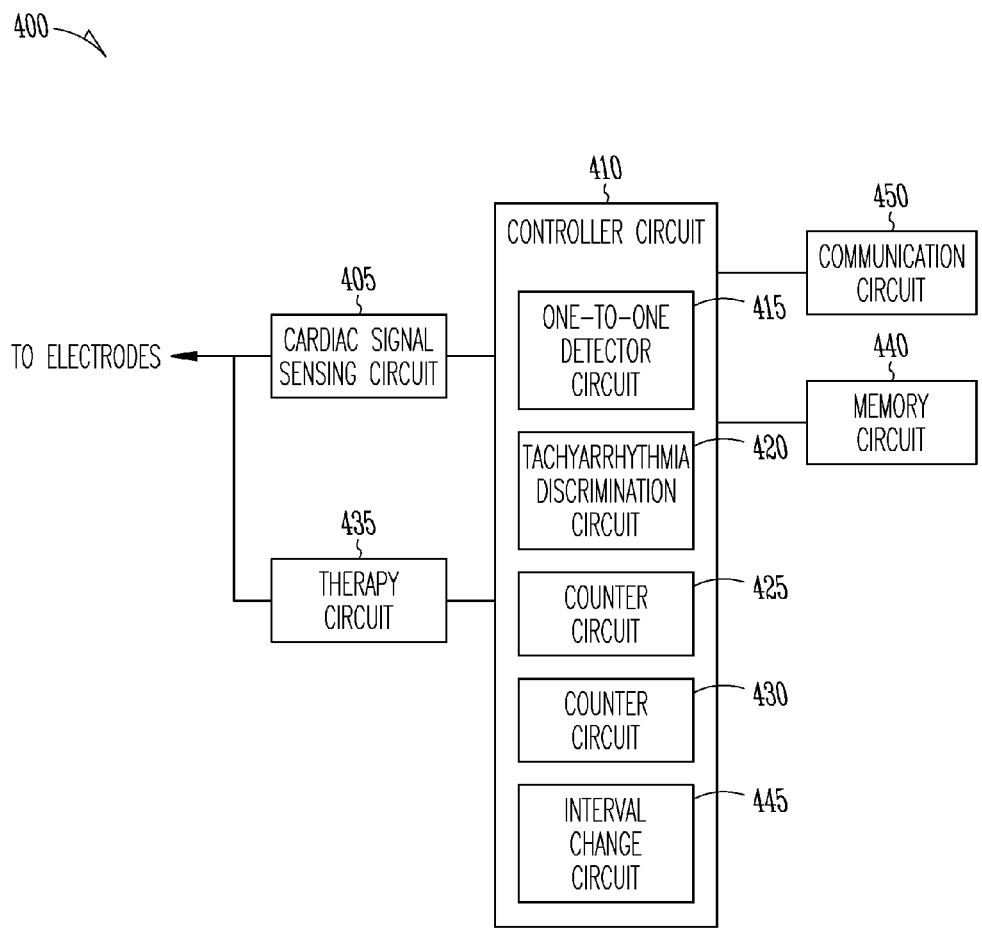
FIG. 4 is a block diagram of portions of an example of a device to classify a detected tachyarrhythmia.

FIG. 4 is a block diagram of portions of an example of a device 400 to classify a detected tachyarrhythmia. The device 400 includes an implantable cardiac signal sensing circuit 405. The cardiac signal sensing circuit 405 provides a sensed depolarization signal from a ventricle and a sensed depolarization signal from an atrium when attached to appropriate electrodes.

The device 400 also includes a controller circuit 410 communicatively coupled to the cardiac signal sensing circuit 405. The communicative coupling allows electrical signals to be communicated between the cardiac signal sensing circuit 405 and the controller circuit 410 even though there may be intervening circuitry.

The controller circuit 410 may include a processor such as a microprocessor, a digital signal processor, application specific integrated circuit (ASIC), microprocessor, or other type of processor, interpreting or executing instructions in software or firmware. The controller circuit 410 includes other circuits or sub-circuits to perform the functions described. These circuits may include software, hardware, firmware or any combination thereof. Multiple functions can be performed in one or more of the circuits as desired.

The controller circuit 410 includes a one-to-one detector circuit 415. The one-to-one detector circuit 415 determines whether a relationship of atrial depolarizations to ventricular depolarizations is substantially one-to-one. In some examples, the one-to-one detector circuit 415 measures sensed cardiac depolarization intervals of the atrium and the ventricle. In certain examples, the one-to-one detector indicates (e.g., generates a signal) that ventricular events occur about one-to-one with atrial events when measured V-V intervals differ from measured A-A intervals by less than a specified threshold interval value.

In some examples, the one-to-one detector monitors (e.g., counts) atrial and ventricular depolarizations during the episode and indicates that ventricular events occur substantially one-to-one with atrial events when the number of ventricular depolarizations differs from the number of atrial depolarizations by less than a specified threshold depolarization difference value. In some examples, the one-to-one detector determines depolarization rate for the atrium and the ventricle, and indicates that the ventricular events occur one-to-one with atrial events when the detected ventricular rate differs from the detected atrial rate by less than a specified rate difference.

The determination of whether an episode is one-to-one may be complicated by the occurrence of premature ventricular contractions (PVCs) and premature atrial contractions (PACs). Typically, the one-to-one detector circuit 415 deems that the relationship of depolarizations is substantially one-to-one during the episode when the difference between the number of atrial depolarizations and the number of ventricular depolarizations is less than a first specified threshold depolarization difference value (e.g., 1 or 2 depolarizations). To allow for PVCs, the one-to-one detector circuit 415 deems that the relationship of depolarizations is substantially one-to-one when the number of ventricular depolarizations is more than a number of detected atrial depolarizations but is less than a second specified threshold depolarization difference value (e.g., 3 or 4 depolarizations). Similarly, to allow for PACs, in some examples the one-to-one detector circuit 415 deems that the relationship of depolarizations is substantially one-to-one when the number of atrial depolarizations is more than a number of detected ventricular depolarizations but is less than a second specified threshold depolarization difference value.

Far-field sensing of events may also complicate the one-to-one determination. Far-field sensing refers to sensing events in a first chamber (e.g., an atrium) that are actually occurring in a second chamber (e.g., a ventricle). Typically, IMDs ignore a depolarization during a device-specified refractory period to avoid cross chamber sensing. However, these depolarizations may be important to a one-to-one determination.

In some examples, the cardiac signal sensing circuit 405 senses a depolarization during the device-specified refractory period. The one-to-one detector circuit 415 includes the depolarization in the one-to-one determination unless determining that the sensed depolarization is a far-field sensed event, in which case the event is ignored. In certain examples, the one-to-one detector circuit 415 determines that a depolarization sensed during the refractory period is far-field when the amplitude of the sensed signal is less than a specified threshold signal amplitude value. In certain examples, the one-to-one detector circuit 415 determines that a depolarization sensed during the refractory period is far-field when the amplitude of the sensed signal is less than other sensed depolarization amplitudes by more than a specified threshold difference value.

The controller circuit 410 also includes a tachyarrhythmia discrimination circuit 420 to detect an episode of tachyarrhythmia. In some examples, the tachyarrhythmia discrimination circuit 420 detects the episode when a determined depolarization rate or interval satisfies a lowest tachyarrhythmia detection threshold rate or longest detection interval. The tachyarrhythmia discrimination circuit 420 uses detected changes in A-A intervals and V-V intervals during the one-to-one episode to classify the tachyarrhythmia. The tachyarrhythmia discrimination circuit 420 may bypass or cancel the one-to-one monitoring when a determined depolarization rate or interval satisfies a ventricular fibrillation detection threshold rate or interval.

When the one-to-one detector circuit 415 indicates that the relationship atrial depolarizations to ventricular depolarizations is substantially one-to-one during the tachyarrhythmia episode, the tachyarrhythmia discrimination circuit 420 classifies the episode as VT when detecting one of a shortening or a prolonging of an A-A interval during the episode that is immediately preceded by the same one of a shortening or prolonging of a V-V interval.

The tachyarrhythmia discrimination circuit 420 classifies the episode as supra-ventricular tachycardia (SVT) when the episode is indicated to be one-to-one and when detecting one of a shortening or prolonging of a V-V interval during the episode that is immediately preceded by the same one of a shortening or prolonging of an A-A interval. As explained previously, in some examples shortening or prolonging of more than one A-A and V-V interval is required before the episode is classified as SVT or VT.

In some examples, the controller circuit 410 includes an interval change circuit 445 for detecting changes in intervals. In some examples, the interval change circuit 445 calculates a difference between consecutive intervals in the atrium and in the ventricle. The interval change circuit indicates a change in A-A or V-V intervals when the measured change exceeds a specified threshold change value (e.g., 20 ms). The interval change circuit 445 may indicate that the change is shortening or prolonging based on whether the calculated difference is a positive or negative quantity.

For instance, the interval change circuit 445 may subtract a current interval from the previous interval. If the magnitude of the calculated interval change between the current interval and the previous interval exceeds the threshold value, and the sign of the calculated difference is negative, the interval change included a prolonging of the intervals. If the sign of the calculated difference is positive, the interval change included a shortening of the intervals. In some examples, the interval change circuit 445 calculates a net interval change over N depolarization intervals, where N is an integer (e.g., 3). The interval change circuit declares a change in the depolarization intervals when the measured total net interval change exceeds the specified threshold change value.

According to some examples, the controller circuit 410 includes a first counter circuit 425 and a second counter circuit 430. The tachyarrhythmia discrimination circuit 420 is configured to increment the first counter 425 when the detected shortening or prolonging of the A-A interval immediately precedes the detected shortening or prolonging of the V-V interval during the episode. This can be thought of as creating a count of SVT indicated events during the episode. This is shown in blocks 510 and 515 of the flow chart in FIG. 5.

The tachyarrhythmia discrimination circuit 420 increments the second counter when the detected shortening or prolonging of the V-V interval immediately precedes the detected shortening or prolonging of the A-A interval during the episode. This can be thought of as creating a count of VT indicated events during the episode. In some examples, the tachyarrhythmia discrimination circuit 420 also requires that the interval from a ventricular depolarization to an atrial depolarization (V-A) interval is greater than a specified threshold V-A interval value (e.g., 100 ms) to increment the second count. This is shown in blocks 520 and 525 of the flow chart of FIG. 5.

Figure 5:
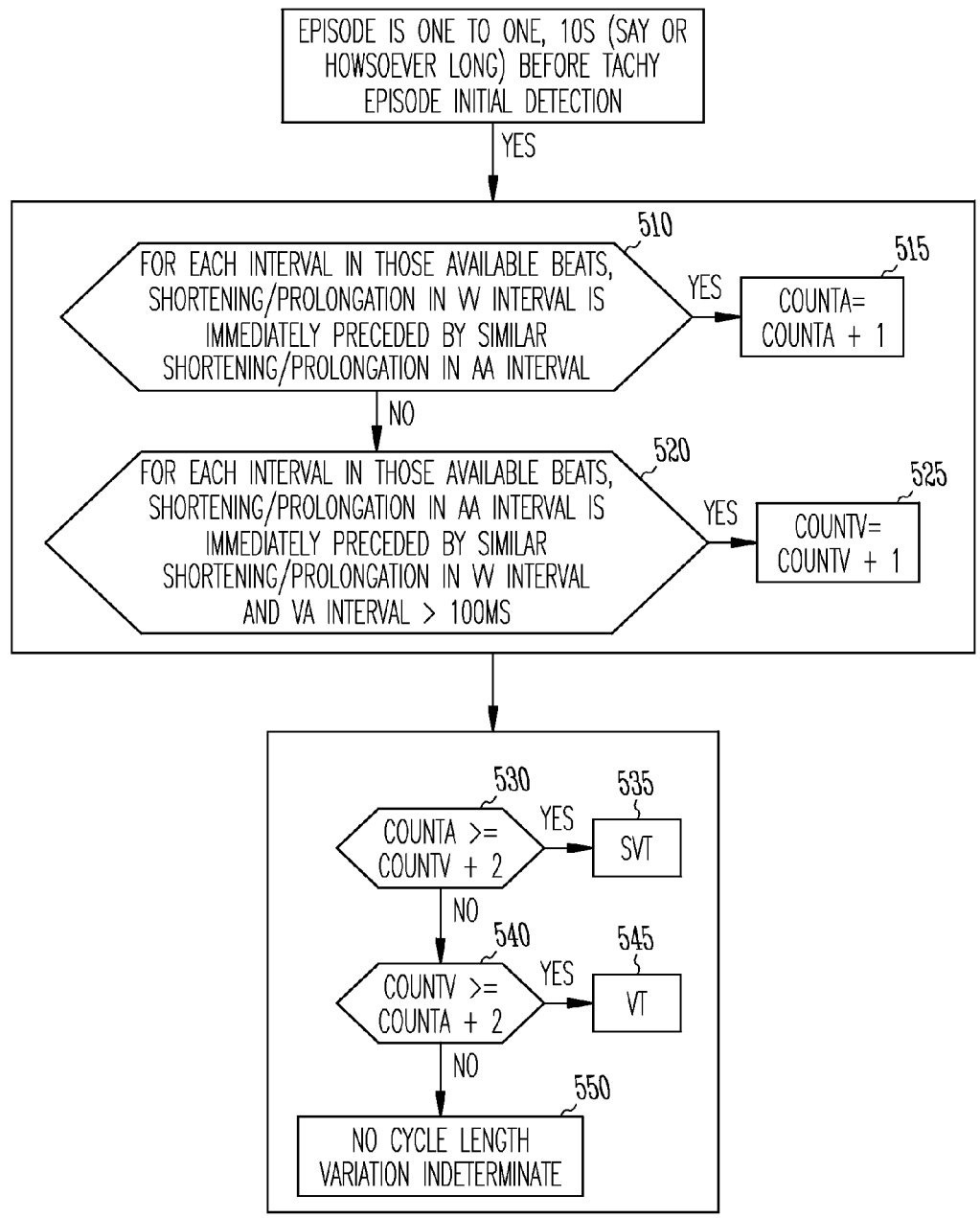
FIG. 5 shows a flow diagram of an example of a method for classifying a tachyarrhythmia episode.

The tachyarrhythmia discrimination circuit 420 classifies the episode as SVT when a count of the first counter 425 exceeds a count of the second counter 430 by a specified threshold count value. For example, as shown in FIG. 5 at blocks 530 and 535, the episode may be classified as SVT when the first counter exceeds the second counter by two counts. The tachyarrhythmia discrimination circuit 420 classifies the episode as VT when the count of the second counter 430 is higher than the count of the first counter 425 by the specified threshold count. For example, as shown in FIG. 5 at blocks 540 and 545, the episode may be classified as SVT when the second counter exceeds the first counter by two counts.

At block 550 of FIG. 5, if no variation in cardiac cycle length is detected, the classification of the episode may be indeterminate. In some examples, if no variation in cardiac cycle length is detected in the episode, tachyarrhythmia discrimination circuit 420 may classify the episode as ST. In some examples, if the detected difference between the V-V interval durations and the A-A interval durations during the tachyarrhythmia episode is less than the specified interval change threshold value, the episode is classified as ST. In some examples, when the episode is classified as ST, other detection enhancements are activated to confirm ST.

In some examples, the device includes a memory circuit 440 integral to or communicatively coupled to the controller circuit 410. A segment of a signal sensed from the ventricle (e.g., a signal sensed over ten seconds time) and a segment of a signal sensed from the atrium may be stored in a buffer in the memory circuit 440. The signal segments stored in the buffer are used by the one-to-one detector circuit 415 and the tachyarrhythmia discrimination circuit 20 to classify the tachyarrhythmia episode.

In some examples, the one-to-one detector circuit 415 monitors cardiac depolarization intervals as they occur in real time and the tachyarrhythmia discrimination circuit 420 classifies the episode in real time. The one-to-one detector circuit 415 may continue the monitoring while the relationship is determined to be substantially one-to-one and a difference between the count of the first counter and the count of the second counter is less than the specified threshold count.

According to some examples, the one-to-one monitoring continues until another indication of tachyarrhythmia occurs, such as when the episode is no longer substantially one-to-one. In some examples, the one-to-one monitoring continues until the detected ventricular rate exceeds the atrial rate by more than a threshold rate value (e.g., more than 10 bpm). In this case the tachyarrhythmia discrimination circuit 420 may classify the detected episode as VT. In some examples, the one-to-one monitoring continues until the detected atrial rate exceeds the ventricular rate by more than a threshold rate value. In this case the tachyarrhythmia discrimination circuit 420 may classify the detected episode as atrial tachyarrhythmia. In some examples, the one-to-one detection continues until the detected episode self-terminates.

In some examples, the controller circuit 410 is configured to initiate storage of at least one of electrograms and markers when at least one of the relationship is determined to be different than substantially one-to-one, or the relationship is determined to be substantially one-to-one and the episode is classified, such as when the difference between the count of the first counter and the count of the second counter exceeds the specified threshold count.

When the episode is classified, the tachyarrhythmia discrimination circuit 420 provides the classification of the tachyarrhythmia episode to a user or process. In some examples, the device 400 includes a therapy circuit 435 to provide one or more of anti-tachyarrhythmia pacing (ATP) therapy or high-energy defibrillation/cardioversion shock therapy to the subject. In some examples, the device 400 includes a switch circuit (not shown) to disconnect the cardiac signal sensing circuit 405 from one or more electrodes during delivery of the therapy to protect the sensing circuitry.

The tachyarrhythmia discrimination circuit 420 may provide the classification to a process executing on the controller circuit 410. The controller circuit 410 may initiate at least one of cardioversion shock therapy, defibrillation shock therapy, and ATP therapy, when the episode is classified as VT. The controller circuit 410 may inhibit therapy or delay therapy if the episode is classified as SVT or ST, such as when the A-A depolarization interval durations and the V-V interval durations remain unchanged during the episode.

In some examples, the device 400 includes a communication circuit 450 In some examples, the process is executing on a remote device. The medical device 400 may include a communication circuit 450 to wirelessly communicate information with the remote device. An approach to communications using an IMD can be found in U.S. Pat. No. 7,664,553, "Systems and Method for Enabling Communications with Implantable Medical Devices," filed Apr. 27, 2005, which is incorporated herein by reference in its entirety.

In some examples, the device 400 communicates a tachyarrhythmia classification to a remote device that includes an IMD programmer. In some examples, the device 400 communicates with the remote device via a third device (e.g., a repeater). In some examples, the remote device is part of an advanced patient management (APM) system, and includes a server connected to a computer network such as the internet for example.

The method of determining whether events in one chamber are driving or influencing the events in the other chamber can be combined with other tachyarrhythmia detection enhancements. In some examples, tachyarrhythmia discrimination circuit 420 detects tachyarrhythmia when the ventricular heart rate exceeds the atrial heart rate (V Rate>A Rate). The tachyarrhythmia discrimination circuit 420 may recurrently update an average ventricular contraction interval (V-V interval) and detects a tachyarrhythmia when the average ventricular depolarization rate exceeds an average atrial depolarization rate by more than a specified rate threshold value. Descriptions of systems and methods for classifying detected tachycardia based on average atrial and ventricular rates calculated from selected atrial and ventricular intervals is found in co-pending U.S. patent application Ser. No. 11/054,726, Elahi et al., entitled, "Method and Apparatus for Rate Accuracy Enhancement in Ventricular Tachycardia Detection," filed Feb. 10, 2005, which is incorporated herein by reference in its entirety.

In another detection enhancement, the tachyarrhythmia discrimination circuit 420 performs a morphology comparison of a sensed cardiac signal to a template of a known morphology (such as normal sinus rhythm) stored in memory. The tachyarrhythmia discrimination circuit 420 can calculate a coefficient of correlation (e.g., a feature correlation coefficient or FCC) that is a measure of similarity between the sensed cardiac signal and the template. If the correlation coefficient indicates a high degree of similarity between the sensed cardiac signal and the template, the sensed rhythm is more likely to be supraventricular rhythm. For instance, if the calculated value of correlation exceeds a specified correlation threshold value, the tachyarrhythmia discrimination circuit 420 classifies an onset episode as SVT.

Examples of methods to discriminate heart rhythms using analysis of the morphology of sensed cardiac signal can be found in Schwartz at al., "Cardiac Rhythm Management Systems and Methods Using Multiple Morphology Templates for Discriminating Between Rhythms," U.S. Pat. No. 7,031,764, filed Nov. 8, 2002 which is incorporated herein by reference in its entirety.

In another example, a template can be generated from a snapshot representative of one of the patient's normal supraventricular conducted beats. Cardiac signals are sensed from pacing leads (rate channel) and shock leads (shock channel). A fiducial point is determined from the signals sensed on the rate channels and is used to align signals sensed on the shock channels. A template for a patient is generated using the aligned shock channel signals. The template is representative of one of the patient's normal supra-ventricular conducted beats. Subsequently detected beats are then used to confirm that the generated template is representative of one of the patient's normal supra-ventricular conducted beats. Systems and methods for generating templates using a snapshot of the patient's normal supra-ventricular conducted beats are described in Kim et al., U.S. Pat. No. 6,708,058, entitled "Normal Cardiac Rhythm Template Generation System and Method," filed Apr. 30, 2001, which is incorporated herein by reference in its entirety.

In another example, a template of a patient's supraventricular rhythm is generated from characterizations performed while the heart is being paced. During the characterization, various pacing parameters are modified and the patient's supraventricular rhythm is characterized while the pacing parameters are modified. Systems and methods for generating a template to represent a patient's supraventricular rhythm are described in Bocek et al., U.S. Pat. No. 6,889,079, entitled "Method and System for Characterizing Supraventricular Rhythm During Cardiac Pacing," filed Apr. 12, 2002, which is incorporated herein by reference in its entirety.

Another tachyarrhythmia detection enhancement is rate stability. In some examples, the tachyarrhythmia discrimination circuit 420 uses an assessment of heart rhythm stability to classify the arrhythmia when a sudden increase in heart rate is detected. Stability in the rhythm with a sudden onset tends to indicate VT while less stability or a more gradual onset may indicate SVT. Examples of methods and systems to detect arrhythmia and assess the stability of the rhythms are found in Gilkerson et al., U.S. Pat. No. 6,493,579, entitled "System and Method for Detection Enhancement Programming," filed Aug. 20, 1999, which is incorporated herein by reference in its entirety.

Another tachyarrhythmia detection enhancement is sustained rate duration (SRD). In some examples, three rate zones are used as a first tier classification of a detected arrhythmia rate into a slow tachycardia (VT-1) zone (e.g., 170-199 bpm, a VT zone (e.g., 200-249 bpm), and a VF zone (e.g., over 250 bpm). The rate zones can be programmable. In SRD detection, the detected rate has to remain in that tachyarrhythmia detection rate zone for a specified duration (e.g., either in seconds or heart beats) to be classified as that type of tachyarrhythmia.

Figure 6:
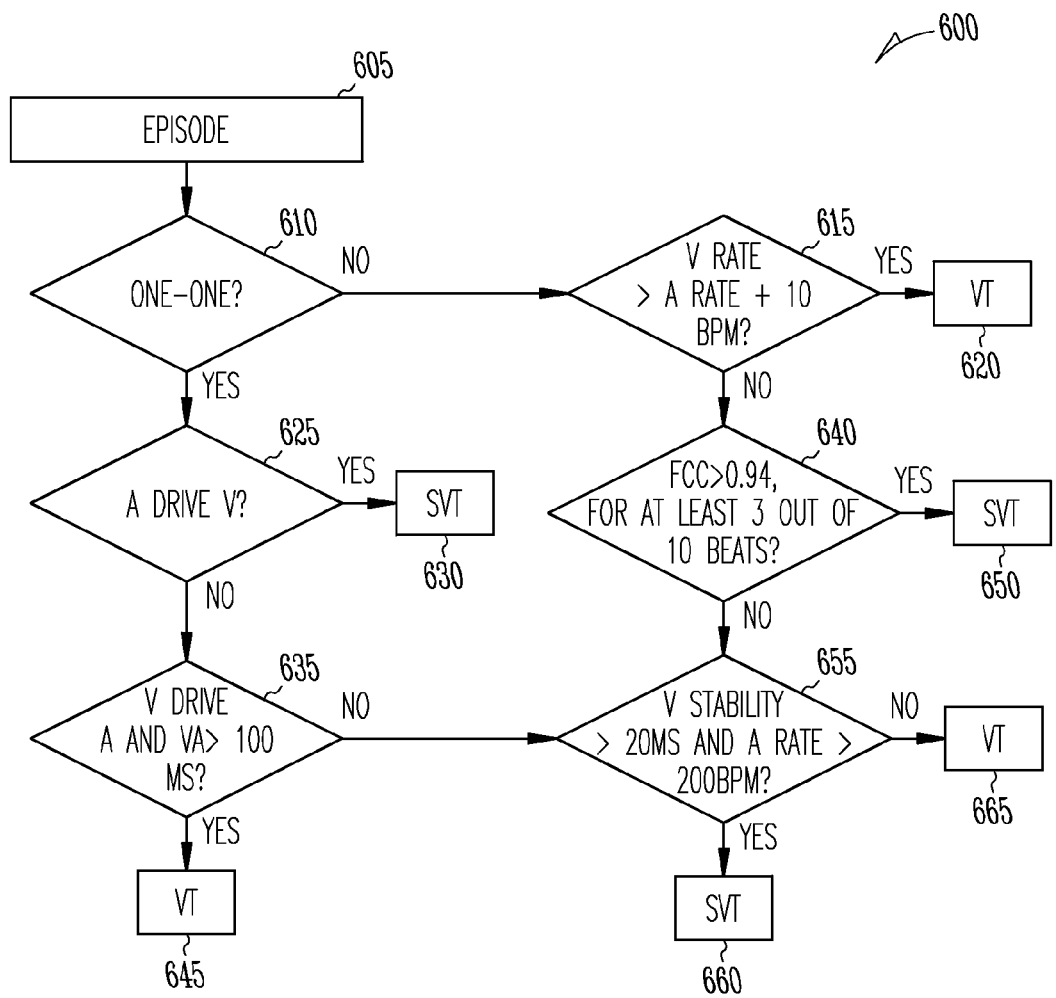
FIG. 6 shows a flow diagram of an example of a method that combines tachyarrhythmia detection enhancements.

FIG. 6 shows a flow diagram of an example of a method 600 that combines tachyarrhythmia detection enhancements. At block 605, an episode of tachyarrhythmia is detected by the tachyarrhythmia discrimination circuit 420. At block 610, the one-to-one detector circuit 415 determines if the episode is substantially one-to-one. If the episode is not substantially one-to-one, the tachyarrhythmia discrimination circuit 420 determines if the V Rate exceeds the A Rate by more than a threshold rate value at block 615. If V Rate does exceed the A Rate by the threshold amount, the tachyarrhythmia discrimination circuit 420 classifies the episode as VT at block 620.

At block 625, if the episode is substantially one-to-one, the tachyarrhythmia discrimination circuit 420 determines if any detected change in the intervals happens in the atrium first. If a detected change occurs and it occurs in the atrium first, the tachyarrhythmia discrimination circuit 420 classifies the episode as SVT at block 630. At block 635, if a detected change occurs, it occurs in the ventricle first, and the V-A interval is greater than a specified threshold value, the tachyarrhythmia discrimination circuit 420 classifies the episode as VT at block 645. If no change in the intervals during the one-to-one episode occurs after a specified period of time, the tachyarrhythmia discrimination circuit 420 may apply further enhanced detection methods to classify the tachyarrhythmia.

At block 640, the tachyarrhythmia discrimination circuit 420 performs a morphology comparison of a sensed cardiac signal to a template. The morphology comparison may include calculation of an FCC, and the stored template may be a representation of NSR. The tachyarrhythmia discrimination circuit 420 determines whether the FCC satisfies a specified FCC threshold (e.g., FCC≧0.94) for a specified number of X beats out of Y beats (e.g., 3 out of 10 beats). If the sensed cardiac signal sufficiently compares to the template of NSR, the tachyarrhythmia discrimination circuit 420 classifies the episode as SVT at block 650. If the conditions of block 640 are not satisfied, the method continues to block 655.

At block 655, the tachyarrhythmia discrimination circuit 420 determines a measure of stability of the ventricular rate. In some examples, if the variation in sensed ventricular depolarizations exceeds a threshold variation threshold value and the atrial rate exceeds a specified atrial rate threshold, the tachyarrhythmia discrimination circuit 420 classifies the episode as SVT at block 660. If the conditions of block 655 are not satisfied, the tachyarrhythmia discrimination circuit 420 classifies the episode as VT at block 665.

The decision blocks on the right of the flow diagram that include V Rate>A Rate, calculate FCC, and determine if V Rate is stable while the A Rate is high can be included in a method of detection referred to as Rhythm ID™. The decision blocks to the left show how one-to-one detection and heart chamber drive can be incorporated into Rhythm ID™.

Figure 7:
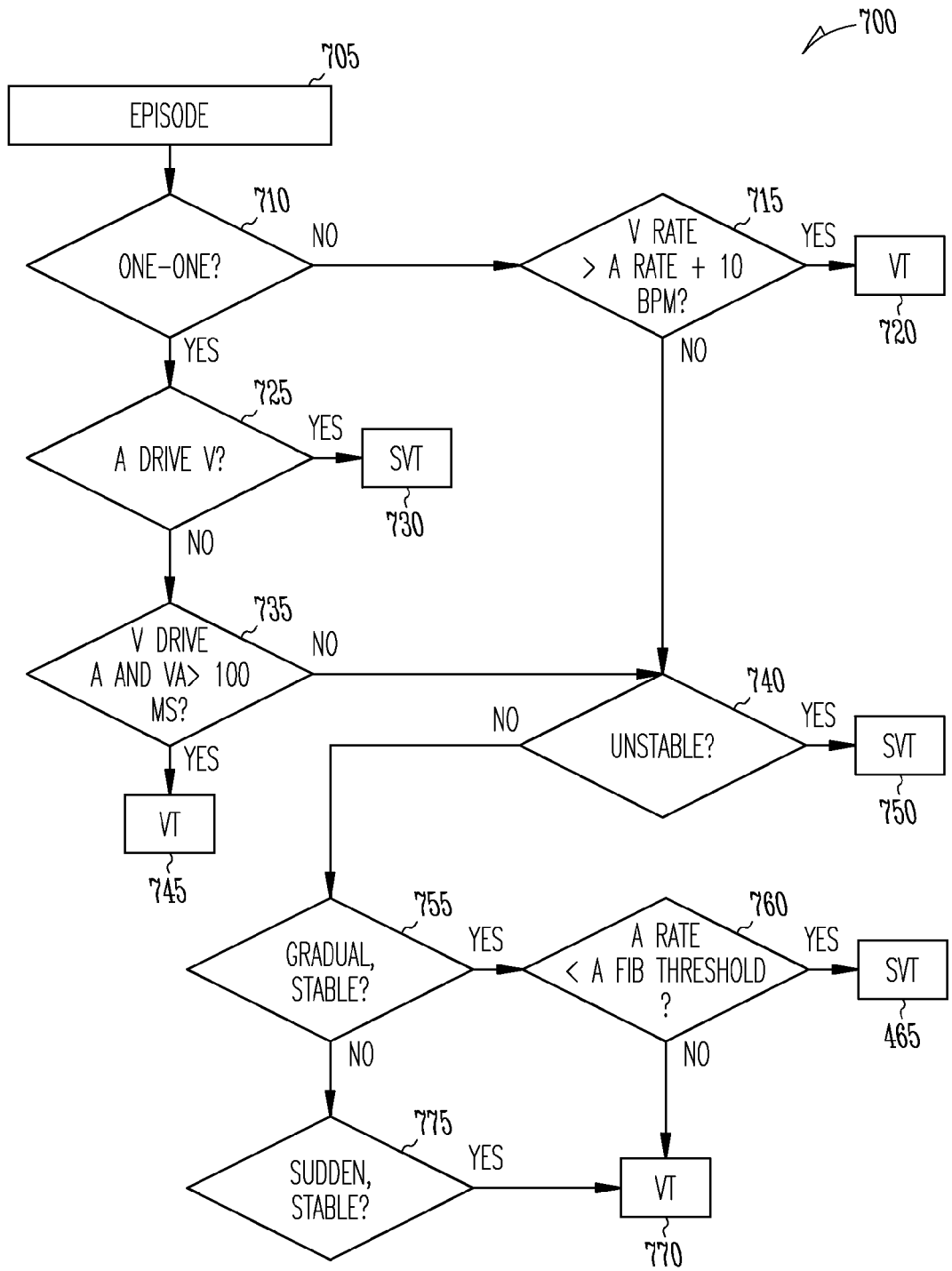
FIG. 7 shows a flow diagram of another example of a method that combines tachyarrhythmia detection enhancements.

FIG. 7 shows a flow diagram of another example of a method 700 that combines tachyarrhythmia detection enhancements. At block 705, an episode of tachyarrhythmia is detected by the tachyarrhythmia discrimination circuit 420. At block 710, the one-to-one detector circuit 415 determines if the episode is substantially one-to-one. If the episode is not substantially one-to-one, the tachyarrhythmia discrimination circuit 420 determines if the V Rate exceeds the A Rate by more than a threshold rate value at block 715. If V Rate does exceed the A Rate by the threshold amount, the tachyarrhythmia discrimination circuit 420 classifies the episode as VT at block 720.

At block 725, if the episode is substantially one-to-one, the tachyarrhythmia discrimination circuit 420 determines if any detected change in the intervals happens in the atrium first. If a detected change occurs and it occurs in the atrium first, the tachyarrhythmia discrimination circuit 420 classifies the episode as SVT at block 730. At block 735, if a detected change occurs, it occurs in the ventricle first, and the V-A interval is greater than a specified threshold value, the tachyarrhythmia discrimination circuit 420 classifies the episode as VT at block 745. If no change in the intervals during the one-to-one episode occurs after a specified period of time, the tachyarrhythmia discrimination circuit 420 may apply further enhanced detection methods to classify the tachyarrhythmia.

At block 740, the tachyarrhythmia discrimination circuit 420 determines a measure of stability of V-V intervals. In some examples, the tachyarrhythmia discrimination circuit 420 measures the differences between V-V intervals. If the V-V intervals are stable then the V-V intervals are uniform and the differences will approach zero. If the V-V intervals are unstable, then the calculated differences will be greater than zero. If the measured differences indicate that the rhythm during the detected episode is unstable, the tachyarrhythmia discrimination circuit 420 classifies the episode as SVT at block 750. If the tachyarrhythmia discrimination circuit 420 determines that the rhythm is stable, the method continues at block 755.

At block 755, if the measured differences indicate that the rhythm during the detected episode is stable and the tachyarrhythmia discrimination circuit 420 determined that an increase in heart rate was gradual rather than sudden, the method proceeds to block 760. At block 760, if the A rate is less than a specified atrial fibrillation detection rate threshold, the tachyarrhythmia discrimination circuit 420 classifies the episode as SVT at block 765. If the A rate is greater than or equal to the atrial fibrillation detection rate threshold, the tachyarrhythmia discrimination circuit 420 classifies the episode as VT at block 770.

At block 775, if the measured differences indicate that the rhythm during the detected episode is stable and the tachyarrhythmia discrimination circuit 420 determined that an increase in heart rate was sudden rather than gradual, the tachyarrhythmia discrimination circuit 420 classifies the episode as VT at block 770.

The decision blocks on the right of the flow diagram that include V Rate>A Rate, the stability determinations, and A Rate<AFib can be included in a method of detection referred to as Onset/Stability™. The decision blocks to the left show how one-to-one detection and heart chamber drive can be incorporated into Onset/Stability™.

Table 1 shows how the detection enhancements can be used with rate detection zones. The rate detection zones can be programmable. The first row of the Table shows how rhythm enhancements can be combined in classifying tachyarrhythmia when three rate zones of VT-1, VT, and VF are used. The Table shows that Rhythm ID™, Onset/Stability™, V Rate>A Rate, SRD, an AFib detection threshold rate, and one-to-one detection with AV drive can be used with detected rates in the VT-1 and VT zones. When the VF rate is detected, the device 400 proceeds to provide therapy without any classification enhancements.

In the second row of the Table, the VT-1 zone is designated as a monitor-only zone. Arrhythmias with rates in monitor-only zone may only cause storage of electrograms to be initiated. In the third row of the Table, only two detection zones VT and VF are used.

When a tachyarrhythmia episode is detected, determining if the episode is one-to-one and monitoring the heart chambers for a change that indicates which chamber is during the tachyarrhythmia can be useful alone in classifying tachyarrhythmia, or can be useful when combined with other tachyarrhythmia detection enhancements.

TABLE 1

|  | VT-1 Zone | VT Zone | VF Zone |
|---|---|---|---|
| 3-zone configuration | Rhythm ID ™ Onset/Stability ™ V > A, SRD, AFib Rate Threshold One-One detection and AV Drive | Rhythm ID ™ Onset/Stability ™ V > A, SRD, AFib Rate Threshold One-One detection and AV Drive | None |
| 3-zone configuration (with Monitor Only zone) | None | Rhythm ID ™ Onset/Stability V > A, SRD, AFib Rate Threshold One-One detection and AV Drive | None |
| 2-zone configuration |  | Rhythm ID ™ Onset/Stability V > A, SRD, AFib Rate Threshold One-One detection and AV Drive | None |

CONCLUSION

Systems and methods for improved discrimination or classification of tachyarrhythmia by a CRM device are described herein.

Example 1 includes subject matter (such as an apparatus) comprising an implantable cardiac signal sensing circuit, configured to provide a sensed depolarization signal from a ventricle and a sensed depolarization signal from an atrium, and a controller circuit communicatively coupled to the implantable cardiac signal sensing circuit. The controller circuit includes a one-to-one detector circuit and a tachyarrhythmia discrimination circuit. The one-to-one detector circuit is configured to measure cardiac depolarization intervals of the atrium and the ventricle and determine whether a relationship of atrial depolarizations to ventricular depolarizations is substantially one-to-one. The tachyarrhythmia discrimination circuit is configured to detect an episode of tachyarrhythmia while the relationship atrial depolarizations to ventricular depolarizations is substantially one-to-one, classify the episode as ventricular tachycardia (VT) when detecting one of a shortening or prolonging of an A-A interval during the episode that is immediately preceded by the same one of a shortening or prolonging of a V-V interval, and provide the classification of the tachyarrhythmia episode to a user or process.

In Example 2, the tachyarrhythmia discrimination circuit of Example 1 is optionally configured to classify the episode as supra-ventricular tachycardia (SVT) when detecting one of a shortening or prolonging of a V-V interval during the episode that is immediately preceded by the same one of a shortening or prolonging of an A-A interval.

In Example 3, the controller circuit of one or any combination of Examples 1 and 2 optionally includes a first counter circuit and a second counter circuit. The tachyarrhythmia discrimination circuit is optionally configured to increment the first counter when the detected shortening or prolonging of the A-A interval immediately precedes the detected shortening or prolonging of the V-V interval during the episode, increment the second counter when the detected shortening or prolonging of the V-V interval immediately precedes the detected shortening or prolonging of the A-A interval during the episode and an interval from a ventricular depolarization to an atrial depolarization (V-A) is greater than a specified threshold V-A interval value, classify the episode as SVT when a count of the first counter exceeds a count of the second counter by a specified threshold count, and classify the episode as VT when the count of the second counter exceeds the count of the first counter by the specified threshold count.

In Example 4, the one-to-one detector circuit of one or any combination of Examples 1-3 is optionally configured to monitor cardiac depolarization intervals as they occur in real time, and continue the monitoring while the relationship is determined to be substantially one-to-one and a difference between the count of the first counter and the count of the second counter is less than the specified threshold count. The controller circuit is optionally configured to initiate storage of at least one of an electrogram and a marker when at least one of the relationship is determined to be different than substantially one-to-one or the relationship is determined to be substantially one-to-one and the difference between the count of the first counter and the count of the second counter exceeds the specified threshold count.

In Example 5, the one-to-one detector circuit of one or any combination of Examples 1-4 is optionally configured to deem that the relationship of atrial depolarizations to ventricular depolarizations is substantially one-to-one when the difference between a number of atrial depolarizations and a number of ventricular depolarizations during the episode is less than a specified threshold depolarization difference value.

In Example 6, the cardiac signal sensing circuit of one or any combination of Examples 1-5 is optionally configured to sense a depolarization during a device-specified refractory period, and wherein the one-to-one detector circuit is configured to include the depolarization in the one-to-one determination unless determining that the sensed depolarization is a far-field sensed event.

In Example 7, the one-to-one detector circuit of one or any combination of Examples 1-6 is optionally configured to deem that the relationship of depolarizations is substantially one-to-one during the episode when the number of atrial depolarizations is more than a number of detected ventricular depolarizations but is less than first specified threshold depolarization difference value and the number of ventricular depolarizations is more than a number of detected atrial depolarizations but is less than a second specified threshold depolarization difference value.

In Example 8, the tachyarrhythmia discrimination circuit of one or any combination of Examples 1-7 is optionally configured to cancel one-to-one monitoring when detecting a depolarization rate or depolarization interval that satisfies a ventricular fibrillation (VF) detection rate threshold or VF detection interval threshold.

In Example 9, the tachyarrhythmia discrimination circuit of one or any combination of Examples 1-8 is optionally configured to detect a tachyarrhythmia episode when a determined depolarization rate or interval satisfies a lowest tachyarrhythmia detection threshold rate or interval.

In Example 10, the subject matter of any or any combination of Examples 1-9 optionally includes a therapy circuit communicatively coupled to the controller circuit and configured to provide at least one of cardioversion shock therapy, defibrillation shock therapy, and anti-tachyarrhythmia pacing (ATP) therapy, and the controller circuit is optionally configured to delay delivery of anti-tachyarrhythmia therapy when A-A depolarization interval durations and V-V interval durations remain unchanged during the episode.

Example 11 can include subject matter, or can optionally be combined with the subject matter of one or any combination of Examples 1-10 to include subject matter (such as a method, a means for performing acts, or a machine-readable medium including instructions that, when performed by the machine, cause the machine to perform acts), comprising monitoring cardiac depolarization intervals in an atrium and in a ventricle of a heart of a subject using an implantable medical device (IMD), detecting an episode of tachyarrhythmia using the IMD, determining that a relationship of atrial (A-A) depolarizations to ventricular (V-V) depolarizations is substantially one-to-one during the episode, classifying the episode as ventricular tachycardia (VT) when detecting one of a shortening or prolonging of an A-A interval during the episode that is immediately preceded by the same one of a shortening or prolonging of a V-V interval, and providing the classification of the tachyarrhythmia episode to a user or process.

In Example 12, the subject matter of Example 11 optionally includes classifying the episode as supra-ventricular tachycardia (SVT) when detecting one of a shortening or prolonging of a V-V interval during the episode that is immediately preceded by the same one of a shortening or prolonging of an A-A interval.

In Example 13, the subject matter of one or any combination of Examples 11 and 12 optionally includes incrementing a first counter when the detected shortening or prolonging of the A-A interval immediately precedes the detected shortening or prolonging of the V-V interval during the episode, and incrementing a second counter when the detected shortening or prolonging of the V-V interval immediately precedes the detected shortening or prolonging of the A-A interval during the episode and an interval from a ventricular depolarization to an atrial depolarization (V-A) is greater than a specified threshold V-A interval value, wherein classifying the episode as VT optionally includes classifying the episode as VT when the count of the second counter is higher than the count of the first counter by a specified threshold count, and wherein classifying the episode as SVT optionally includes classifying the episode as SVT when a count of the first counter is higher than a count of the second counter by the specified threshold count.

In Example 14, the subject matter of one or any combination of Examples 11-13 optionally includes monitoring cardiac depolarization intervals as they occur in real time, continuing the monitoring while the relationship is determined to be substantially one-to-one and a difference between counts of the first counter circuit and the second counter circuit is less than the specified threshold count, and initiating storage of at least one of an electrogram and a marker when at least one of the relationship is determined to be different than substantially one-to-one or the relationship is determined to be substantially one-to-one and the difference between the count of the first counter and the count of the second counter satisfies the specified threshold count.

In Example 15, the determining a relationship of atrial depolarizations to ventricular depolarizations of one or any combination of Examples 11-14 optionally includes deeming that the relationship is substantially one-to-one when the difference between a number of atrial depolarizations and a number of ventricular depolarizations during the episode is less than a specified threshold depolarization difference value.

In Example 16, the subject matter of one or any combination of examples 11-15 optionally includes sensing a depolarization during a device refractory period; and including the depolarization in the one-to-one determination unless determining that the sensed depolarization is a far-field sensed event.

In Example 17, the deeming that the relationship is substantially one-to-one of one or any combination of Examples 11-16 optionally includes deeming that the relationship is substantially one-to-one when the number of atrial depolarizations is more than the number of ventricular depolarizations but is less than a first specified threshold depolarization difference value, and deeming that the relationship is substantially one-to-one when the number of ventricular depolarizations is more than the number of atrial depolarizations but is less than a second specified threshold depolarization difference value.

In Example 18, the subject matter of one or any combination of Examples 11-17 optionally includes calculating a net change over N depolarization intervals, where N is an integer, and declaring a change in a depolarization interval when the calculated total net interval change exceeds a specified threshold value.

In Example 19, the detecting an episode of tachyarrhythmia of one or any combination of Examples 11-18 optionally includes detecting a tachyarrhythmia episode when a determined depolarization rate or interval satisfies a lowest tachyarrhythmia detection threshold rate or interval.

In Example 20, the subject matter of one or any combination of Examples 11-19 optionally includes delaying anti-tachyarrhythmia therapy when A-A depolarization interval durations and V-V interval durations remain unchanged during the episode.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable cardiac signal sensing circuit, configured to provide a sensed depolarization signal from a ventricle and a sensed depolarization signal from an atrium; and
   a controller circuit communicatively coupled to the implantable cardiac signal sensing circuit, wherein the controller circuit includes:
      a one-to-one detector circuit configured to:
         measure cardiac depolarization intervals of the atrium and the ventricle; and
         determine whether a relationship of atrial (A-A) depolarizations to ventricular (V-V) depolarizations is substantially one-to-one;
      a first counter circuit and a second counter circuit; and
      a tachyarrhythmia discrimination circuit configured to:
         detect an episode of tachyarrhythmia while the relationship atrial depolarizations to ventricular depolarizations is substantially one-to-one;
         increment the first counter when detecting one of a shortening or prolonging of a V-V interval that is immediately preceded by the same one of a detected shortening or prolonging of an A-A interval during the episode;
         increment the second counter when detecting one of a shortening or prolonging of an A-A interval during the episode that is immediately preceded by the same one of a shortening or prolonging of a V-V interval and an interval from a ventricular depolarization to an atrial depolarization (V-A) is greater than a specified threshold V-A interval value;
         classify the episode as VT when the count of the second counter exceeds the count of the first counter by a specified threshold count; and
         provide the classification of the tachyarrhythmia episode to a user or process.

2. The apparatus of claim 1, wherein the tachyarrhythmia discrimination circuit configured to classify the episode as SVT when a count of the first counter exceeds a count of the second counter by the specified threshold count.

3. The apparatus of claim 1,
   wherein the one-to-one detector circuit is configured to:
      monitor cardiac depolarization intervals as they occur in real time;
      continue the monitoring while the relationship is determined to be substantially one-to-one and a difference between the count of the first counter and the count of the second counter is less than the specified threshold count; and
   wherein the controller circuit is configured to initiate storage of at least one of an electrogram and a marker when at least one of the relationship is determined to be different than substantially one-to-one or the relationship is determined to be substantially one-to-one and the difference between the count of the first counter and the count of the second counter exceeds the specified threshold count.

4. The apparatus of claim 1, wherein the one-to-one detector circuit is configured to deem that the relationship of atrial depolarizations to ventricular depolarizations is substantially one-to-one when the difference between a number of atrial depolarizations and a number of ventricular depolarizations during the episode is less than a specified threshold depolarization difference value.

5. The apparatus of claim 4, wherein the cardiac signal sensing circuit is configured to sense a depolarization during a device-specified refractory period, and wherein the one-to-one detector circuit is configured to include the depolarization in the one-to-one determination unless determining that the sensed depolarization is a far-field sensed event.

6. The apparatus of claim 4, wherein the one-to-one detector circuit is configured to deem that the relationship of depolarizations is substantially one-to-one during the episode when:
the number of atrial depolarizations is more than a number of detected ventricular depolarizations but is less than first specified threshold depolarization difference value; and
the number of ventricular depolarizations is more than a number of detected atrial depolarizations but is less than a second specified threshold depolarization difference value.

7. The apparatus of claim 1, wherein the one-to-one detector circuit is configured to deem that the relationship of atrial depolarizations to ventricular depolarizations is substantially one-to-one when the detected ventricular rate differs from the detected atrial rate by less than a specified rate difference.

8. The apparatus of claim 1, wherein the tachyarrhythmia discrimination circuit cancels one-to-one monitoring when detecting a depolarization rate or depolarization interval that satisfies a ventricular fibrillation (VF) detection rate threshold or VF detection interval threshold.

9. The apparatus of claim 1, wherein the tachyarrhythmia discrimination circuit is configured to detect a tachyarrhythmia episode when a determined depolarization rate or interval satisfies a lowest tachyarrhythmia detection threshold rate or interval.

10. The apparatus of claim 1, including a therapy circuit communicatively coupled to the controller circuit and configured to provide at least one of cardioversion shock therapy, defibrillation shock therapy, and anti-tachyarrhythmia pacing (ATP) therapy, and
wherein the controller circuit is configured to delay delivery of anti-tachyarrhythmia therapy when A-A depolarization interval durations and V-V interval durations remain unchanged during the episode.

11. A method comprising:
monitoring cardiac depolarization intervals in an atrium and in a ventricle of a heart of a subject using an implantable medical device (IMD);
detecting an episode of tachyarrhythmia using the IMD;
determining that a relationship of atrial (A-A) depolarizations to ventricular (V-V) depolarizations is substantially one-to-one during the episode;
incrementing a first counter when detecting one of a shortening or prolonging of an A-A interval that immediately precedes the same one of a shortening or prolonging of the V-V interval during the episode;
incrementing a second counter when detecting one of a shortening or prolonging of a V-V interval that immediately precedes the same one of a shortening or prolonging of the A-A interval during the episode and an interval from a ventricular depolarization to an atrial depolarization (V-A) is greater than a specified threshold V-A interval value;
classifying the episode as ventricular tachycardia (VT) when the count of the second counter exceeds the count of the first counter by a specified threshold count; and
providing the classification of the tachyarrhythmia episode to a user or process.

12. The method of claim 11, including:
classifying the episode as supra-ventricular tachycardia (SVT) when a count of the first counter exceeds a count of the second counter by a specified threshold count.

13. The method of claim 11, including:
monitoring cardiac depolarization intervals as they occur in real time;
continuing the monitoring while the relationship is determined to be substantially one-to-one and a difference between counts of the first counter circuit and the second counter circuit is less than the specified threshold count; and
initiating storage of at least one of an electrogram and a marker when at least one of the relationships is determined to be different than substantially one-to-one or the relationship is determined to be substantially one-to-one and the difference between the count of the first counter and the count of the second counter satisfies the specified threshold count.

14. The method of claim 11, wherein determining a relationship of atrial depolarizations to ventricular depolarizations includes deeming that the relationship is substantially one-to-one when the difference between a number of atrial depolarizations and a number of ventricular depolarizations during the episode is less than a specified threshold depolarization difference value.

15. The method of claim 14, including:
sensing a depolarization during a device refractory period; and
including the depolarization in the one-to-one determination unless determining that the sensed depolarization is a far-field sensed event.

16. The method of claim 14, wherein deeming that the relationship is substantially one-to-one includes:
deeming that the relationship is substantially one-to-one when the number of atrial depolarizations is more than the number of ventricular depolarizations but is less than a first specified threshold depolarization difference value; and
deeming that the relationship is substantially one-to-one when the number of ventricular depolarizations is more than the number of atrial depolarizations but is less than a second specified threshold depolarization difference value.

17. The method of claim 11, wherein determining a relationship of atrial depolarizations to ventricular depolarizations includes deeming that the relationship is substantially one-to-one when the detected ventricular rate differs from the detected atrial rate by less than a specified rate difference.

18. The method of claim 11, including:
calculating a net change over N depolarization intervals, where N is an integer; and
declaring a change in a depolarization interval when the calculated total net interval change exceeds a specified threshold value.

19. The method of claim 11, wherein detecting an episode of tachyarrhythmia includes detecting a tachyarrhythmia episode when a determined depolarization rate or interval satisfies a lowest tachyarrhythmia detection threshold rate or interval.

20. The method of claim 11, including delaying anti-tachyarrhythmia therapy when A-A depolarization interval durations and V-V interval durations remain unchanged during the episode.

* * * * *